(12) United States Patent
Romo, Jr. et al.

(10) Patent No.: US 11,964,061 B2
(45) Date of Patent: Apr. 23, 2024

(54) METHOD OF PRODUCING A CUSTOM ORTHOSIS FOR A PATIENT

(71) Applicant: Aspen Medical Products, LLC, Irivne, CA (US)

(72) Inventors: Harry Duane Romo, Jr., Aliso Viejo, CA (US); Frank Hernandez, Rancho Mission Viejo, CA (US); Joel Perez, Long Beach, CA (US)

(73) Assignee: Aspen Medical Products, LLC, Irvine, CA (US)

( * ) Notice: Subject to any disclaimer, the term of this patent is extended or adjusted under 35 U.S.C. 154(b) by 0 days.

(21) Appl. No.: 17/178,071

(22) Filed: Feb. 17, 2021

(65) Prior Publication Data
US 2022/0257824 A1    Aug. 18, 2022

(51) Int. Cl.
*B29C 39/10* (2006.01)
*A61L 15/12* (2006.01)
(Continued)

(52) U.S. Cl.
CPC .............. *A61L 15/14* (2013.01); *A61L 15/125* (2013.01); *B29C 39/10* (2013.01); *D04B 1/265* (2013.01);
(Continued)

(58) Field of Classification Search
CPC ..................................................... B29C 39/10
See application file for complete search history.

(56) References Cited

U.S. PATENT DOCUMENTS 3,286,277 A    11/1966   Weiss
4,240,415 A *  12/1980   Wartman ................ A61L 15/12
                                                     602/14
(Continued)

FOREIGN PATENT DOCUMENTS

FR      3018043      *   9/2015
GB      1253651 A        11/1971
(Continued)

OTHER PUBLICATIONS

PCT/US2022/016874 filed Feb. 17, 2022 International Search Report and Wirtten Opinion dated Jul. 19, 2022.
(Continued)

*Primary Examiner* — Edmund H Lee
(74) *Attorney, Agent, or Firm* — Rutan & Tucker, LLP

(57) ABSTRACT

An orthopedic precast comprises a knitted shell portion and a knitted flexible portion. The precast is positioned about a limb or other mold, and heat or other hardening agent is used to harden the shell portion, while retaining flexibility in the flexible portion. Contemplated hardening agents include light, heat, and chemical polymerizing agents. In some embodiments the shell portion includes threads or yarns comprising a thermoplastic, which is then hardened by heating the thermoplastic sufficiently to at least partially melt, and thereby fuse together some of the threads or yarns, and then cooling to ambient temperature. In other embodiments, the precast is contained in a bag or other airtight container, along with a self-heating composition that is triggered to release heat upon contact with oxygen. In still other embodiments, the precast includes a prepolymer of other polymerizable composition, which is polymerized by effective application of light, heat, and/or chemical agent(s).

18 Claims, 16 Drawing Sheets

(51) Int. Cl.
*A61L 15/14* (2006.01)
*D04B 1/26* (2006.01)
*A61F 5/01* (2006.01)
*B29L 31/00* (2006.01)

(52) U.S. Cl.
CPC ............ *A61F 5/0111* (2013.01); *A61F 5/0118* (2013.01); *B29L 2031/753* (2013.01); *D10B 2509/00* (2013.01)

(56) References Cited

U.S. PATENT DOCUMENTS

| | | | |
|---|---|---|---|
| 4,483,333 A * | 11/1984 | Wartman | A61L 15/125 |
| | | | 602/7 |
| 4,745,912 A | 5/1988 | McMurray | |
| 6,093,161 A * | 7/2000 | Vlaeyen | A61F 5/05 |
| | | | 602/5 |
| 7,905,848 B2 | 3/2011 | Cuypers et al. | |
| 8,303,527 B2 * | 11/2012 | Joseph | A61F 5/0111 |
| | | | 602/8 |
| 8,480,604 B2 | 7/2013 | Messer | |
| 8,959,959 B1 | 2/2015 | Podhajny | |
| 9,452,073 B2 | 9/2016 | Cuypers et al. | |
| 9,572,703 B2 | 2/2017 | Matthews | |
| 10,081,889 B2 | 9/2018 | Cuypers et al. | |
| 10,343,309 B2 | 7/2019 | Cuypers et al. | |
| 10,750,826 B2 | 8/2020 | Meythaler et al. | |
| 10,765,773 B2 * | 9/2020 | Watson | A61F 13/04 |
| 10,864,099 B2 | 12/2020 | Cuypers et al. | |
| 2002/0088501 A1 | 7/2002 | Bruner | |
| 2002/0182961 A1 | 12/2002 | Clercq et al. | |
| 2004/0118018 A1 | 6/2004 | Dua | |
| 2006/0253960 A1 | 11/2006 | Horn et al. | |
| 2010/0199520 A1 | 8/2010 | Dua et al. | |
| 2012/0210488 A1 | 8/2012 | Blakely et al. | |
| 2013/0025075 A1 | 1/2013 | Meschter et al. | |
| 2013/0260629 A1 | 10/2013 | Dua et al. | |
| 2016/0286898 A1 | 10/2016 | Manz et al. | |
| 2018/0127905 A1 | 5/2018 | Amis et al. | |
| 2018/0169963 A1 | 6/2018 | Dua et al. | |
| 2018/0317592 A1 | 11/2018 | Rudolf et al. | |
| 2018/0332920 A1 | 11/2018 | Burch | |
| 2019/0208862 A1 | 7/2019 | Poegl et al. | |
| 2019/0343216 A1 | 11/2019 | Huffa et al. | |
| 2019/0387813 A1 | 12/2019 | Almog | |
| 2020/0009288 A1 * | 1/2020 | Geremtzes | A61L 15/12 |
| 2020/0022457 A1 | 1/2020 | Oordt et al. | |
| 2020/0375317 A1 | 12/2020 | Meir | |
| 2021/0030117 A1 | 2/2021 | Frazier et al. | |
| 2021/0153602 A1 | 5/2021 | Polgar et al. | |
| 2022/0256939 A1 | 8/2022 | Romo, Jr. et al. | |

FOREIGN PATENT DOCUMENTS

| | | | |
|---|---|---|---|
| JP | H0370558 | * | 3/1991 |
| JP | 2004313385 | * | 11/2004 |
| JP | 2004339651 | * | 12/2004 |

OTHER PUBLICATIONS

U.S. Appl. No. 17/673,716, filed Feb. 16, 2022 Non-Final Office Action dated Oct. 2, 2023.

* cited by examiner

METHOD OF PRODUCING A CUSTOM ORTHOSIS FOR A PATIENT

BACKGROUND

The field of the invention is orthopedic braces (orthoses).

The following description includes information that may be useful in understanding the present invention. It is not an admission that any of the information provided herein is prior art or relevant to the presently claimed invention, or that any publication specifically or implicitly referenced is prior art.

Orthopedic braces (orthoses) usually need to be adjusted or customized in some manner to conform to the body part(s) being braced, and then properly positioned. A typical orthosis commonly has at least two portions, a rigid portion supporting a body part, and a flexible portion securing the orthosis to the body. The flexible portion is often a strap, and in many orthoses, multiple straps are required to adequately secure the orthosis. It can be time-consuming for a patient to repeatedly have to adjust the different straps.

U.S. Pat. No. 8,480,604 to Messer describes an ankle foot orthosis (AFO) which has a strap positioned around a calf region. Unfortunately, for some individuals a single strap might not be sufficient to secure the orthosis, given the complex ankle movements including dorsiflexion, plantarflexion, inversion, and eversion that occur during walking. Thus, the AFO could be mispositioned during walking, providing a painful walking experience to the patient, and even potentially worsening a patient's medical condition.

U.S. Pat. No. 9,572,703 to Matthews describes an orthosis sock that utilizes a resilient material for restricting movement of a wearer's foot. Because the orthosis is a sock, it is relatively easier to wear than a typical AFO. However, resiliency of the material can be insufficient to provide adequate support.

It is known to create custom AFOs by creating a negative mold of a patient's lower leg, ankle, and foot, using the negative mold to create a positive mold, wrapping preheated flexible and hardenable materials about different portions of the positive mold, and then applying vacuum to the material-wrapped positive mold then allowing time for the materials to cool to the shape of the positive mold. Once cooled, the materials must be carefully cut off the model then all cut edges must be ground/smoothed to the final shape. Production of such custom AFOs is extremely manual and inefficient. Production is time consuming, requires considerable skill, and is therefore relatively expensive.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Thus, there is still a need for systems and methods for efficiently producing custom orthoses.

SUMMARY OF THE INVENTION

The inventive subject matter provides systems and methods in which a knitted orthopedic precast/orthosis has (a) a shell portion comprising a knitted strand of at least a first thermoplastic material; mechanically coupled with (b) a flexible portion including a knitted strand of a non-thermoplastic material.

As used herein, the terms "rigid" or "rigidity" with respect to an object or portion of an object means that the object or rigid portion will resist bending or deformation. According to this definition, different lengths of a given structure and composition can be rigid at a shorter length, and flexible at a longer length. As used herein, the terms "very rigid" or "high rigidity" with respect to an object or portion of an object means that the object or rigid portion will be permanently deformed if bent or twisted by at least 20° end to end.

As used herein, the term "resilient" with respect to an object or a portion of an object means that upon bending or stretching, the portion will automatically return to its substantially pre-bent ore pre-stretched shape. As used herein the term "bending" should be construed to include twisting.

As used herein, the term "flexible" with respect to an object or a portion of an object means that the flexible portion will not be permanently deformed by bending or twisting. As used herein, the term "permanently deformed" means that deformation remains unless the deformation is actively repaired. According to this definition, an object or a portion of an object could be rigid in one direction, and flexible in another direction. Unless otherwise specified in such cases, the object or portion of the object is deemed to be rigid.

As used herein, the term "elastic" with respect to an object or portion of an object means that if the elastic portion is stretched or compressed lengthwise by at least 10%, it will return to its resting length, without the need for application of an external force, and without permanent deformation.

As used herein, the term "shell" means a structure having a cavity, hollow, or lumen configured to impart rigidity that restrains movement of a part of a patient's body, wherein the structure is either rigid or will become rigid upon application of heat and cooling.

As used herein the term "patient" includes both humans and animals, independently of whether the patient is under the care of a medical or veterinary professional.

As used herein, the term "strand" means an elongate, thin length of one or more natural, artificial, or combined natural and artificial substances, collectively no more than 3 mm thick over a length of at least 1 cm. Strands includes threads and yarns.

In some embodiments, an orthopedic precast/orthosis is configured to have a tube that includes both the shell and flexible portions.

In some embodiments, the shell portion orients lengthwise along the tube. For example, the shell and flexible portions of a precast could correspond to the anterior and posterior portions of a lower leg respectively, and these portions can be directly connected to each other. For such a precast, the shell portion would be considered to be oriented lengthwise along the tube.

Alternatively, a shell portion can orient crosswise with respect to a tube. For example, a precast capable of accommodating a torso portion of a patient could have a shell portion that extends across the front of a patient, and flexible portions that also extend across the front of the patient, connected superiorly and inferiorly to the shell portion. For such a precast, the shell portion would be considered to be oriented crosswise along the tube.

As used herein, the term "crosswise" includes various degrees of diagonality.

A thermoplastic material used in a shell portion can be different from or the same as a thermoplastic material used in an additional shell portion. For example, the thermoplastic material used in a wrist part of a full arm wrist orthosis can be the same as or different from the thermoplastic material used in an elbow part. In preferred embodiments, the melting temperatures of different thermoplastic materials used in the same precast differ by 10°-20 C, by 10°-30° C., 30°-50° C., and even between 50°-150° C.

In some embodiments, the thermoplastic portion can comprise at least 30 wt % of a precast. In a preferred embodiment, the thermoplastic portion can comprise between 5 wt % and 90 wt % of the precast, more preferably between 50 wt % and 90 wt % of the precast, still more preferably between 80 wt % and 90 wt % of the precast.

Similarly, in some embodiments, the shell portion can comprise at least 30 wt % of a precast. In a preferred embodiment, the shell portion can comprise between 5 wt % and 90 wt % of the precast, more preferably between 50 wt % and 90 wt % of the precast, still more preferably between 80 wt % and 90 wt % of the precast.

In some embodiments, a shell portion of the precast can vary in nominal thickness by at least 50%. Similarly, a flexible portion of a precast can vary in nominal thickness by at least 50%.

In some embodiments, the flexible portion can be elastic. The elasticity can be achieved by a material itself having an elastic feature or knitting techniques being capable of having an elastic feature.

In some embodiments, the shell and flexible portion can be layered. For example, the flexible portion can be laminated with at least a layer of the shell portion to provide structural reinforcement. Alternatively, a shell portion can be laminated with at least one layer of a flexible portion to enhance skin comfort.

In some embodiments, a precast can include at least an eye and a mateable strap.

The inventive subject matter also includes methods of producing a custom orthosis, including the steps of:
1. Placing an orthopedic precast about a positive mold, the precast including a) a shell portion that includes a knitted strand of at least a first thermoplastic material that melts at a first melting point, and b) a flexible portion that includes an elastic, knitted strand that does not melt below the first melting point; and
2. Heating the precast to at least 140° C. to partially melt and thereby fuse and rigidify the shell portion. Other contemplated minimum heating temperatures are set forth according to thermoplastics in the table below. One of ordinary skill in the art would appreciate that raising the temperature to completely melt a thermoplastic would result in loss of functional shape of the shell portion, and therefore the processing temperature should be raised to only a lower part of the melting range. Also, the processing temperature should be raised at a speed at which the surface of the thermoplastic material has begun to melt, but the core of the thermoplastic material retains its shape. It's also contemplated that where there are different layers of thermoplastic material in the shell portion, the temperature parameters could be utilized such that the thermoplastic in some of the layers some of the layers melts more than the thermoplastic in others of the layers. Experimentation has demonstrated that one successful method of implementing the inventive subject matter herein, is to provide a positive mold with through holes, and steam the precast from the inside, through the positive mold.

Examples of thermoplastic with melting point temperature ranges can be found at https://www.plastikcity.co.uk/useful-stuff/material-melt-mould-temperatures, and http://polymerdatabase.com/polymer%20physics/Polymer%20Tm%20C.html.

Positive molds of a body part can be produced according to well-known techniques, including (a) using plaster or other materials to produce a negative cast of a body part, removing the negative cast from the body part, filing the cast with a hardenable casting material, and then removing the negative cast from about what is then the positive mold. It is also known to cut away or add material to the positive mold. Positive molds can be made from any body part or combination of adjoining parts, for example a positive mold could be made that mimics a hand, wrist and forearm.

In preferred methods the precast is somewhat tubular, with one or two open ends so that the precast can be pulled over a body part. In some embodiments the shell can include second or third thermoplastic materials with different melting points from the first thermoplastic material.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Various objects, features, aspects and advantages of the inventive subject matter will become more apparent from the following detailed description of preferred embodiments, along with the accompanying drawing figures in which like numerals represent like components.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

The recitation of ranges of values herein is merely intended to serve as a shorthand method of referring individually to each separate value falling within the range. Unless otherwise indicated herein, each individual value is incorporated into the specification as if it were individually recited herein.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Figure 1:
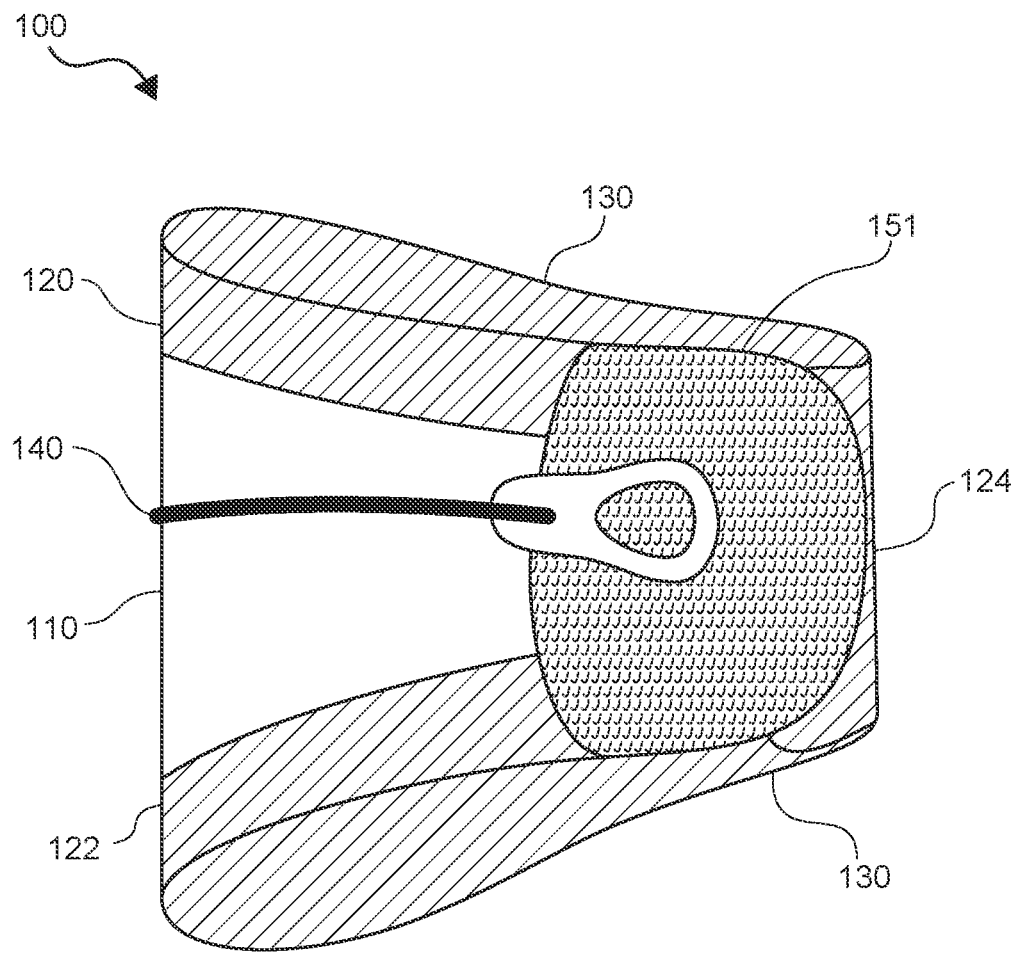
FIG. 1 is a perspective view of a precast for a torso orthosis.

FIG. 1 generally depicts a precast 100, sized and dimensioned to wrap about a torso of a patient. The precast has a shell portion 110 knitted with one or more strands comprising a thermoplastic material positioned between upper and lower flexible portions 120 and 122. The upper and lower flexible portions 120 and 122 are knitted with one or more strands comprising a non-thermoplastic material. The shell 110 and flexible portions 120, 122 generally compose a tube 130, with two open ends. In this particular example, both the shell 110 and the flexible portions 120, 122 are oriented crosswise with respect to the tube 130.

The one or more strands of the shell portion include at least one thermoplastic material, and can also be a composite, which includes at least two different thermoplastic materials. The various thermoplastic materials can have the same or a different melting temperature. Strands can also be a composite of one or more thermoplastic materials and one or more non-thermoplastic materials. The thermoplastic and non-thermoplastic materials can be selected using any combination of natural and synthetic materials to accomplish a desired characteristic, as for example, a desired degree of stiffness, compressibility, flexibility, bending, stretch, and resilience.

Preferred thermoplastic materials form flexible strands at room temperature, are non-toxic, melt between 140° C. and 350° C., and become rigid when strands are partially melted together into a sheet or mat having a thickness of 0.5 mm-6 mm. Contemplated thermoplastic materials include Polyethylene Terephthalate (PET), Polyether ether ketone (PEEK) Polyphenylene oxide (PPO), Polypropylene (PP), polyethylene (PE), polyvinyl chloride (PVC) and polystyrene (PS), poly(methyl methacrylate) (PMMA), Acrylonitrile butadiene styrene (ABS), Polylactic acid (PLA), Polybenzimidazole (PBI), Polycarbonate (PC), Polyether sulfone (PES), Polyoxymethylene (POM), Polyphenylene sulfide (PPS), Polystyrene, Polyvinyl chloride (PVC), Polyvinylidene fluoride (PVDF), Polytetrafluoroethylene (PTFE), Polyamide 6 (PA6), Polybutylene terephthalate (PBT), Polyetherimide (PEI).

The one or more strands of the rigid portion can comprise thermoplastic and non-thermoplastic materials. For example, a PET strand could include Kevlar™, carbon fibers, nanotubes, glass fibers, ceramic, and/or metal fibers.

The one or more strands of the flexible portion can also comprise thermoplastic and/or non-thermoplastic materials, as long as no substantial quantity of such materials melt below the melting point of a substantial quality of the lowest-melting thermoplastic material used in the shell portion. One of the inventive concepts is that a precast will have (1) one or more knitted strands of a first material or set of materials, which upon heating, partially melt and therefore fuse together to form a rigid shell, and (2) one or more knitted strands of a different material or materials that remain flexible upon cooling, either because they do not melt, or they melt to an insubstantial amount at the temperature used to melt the shell materials. Accordingly, the terms "insubstantial" and "substantial" are used herein in that context.

It should be appreciated then, that the one or more knitted strands of a different material or materials that remain flexible upon cooling might or might not include a thermoplastic material. Preferably, however, the one or more knitted strands of a different material or materials that remain flexible upon cooling could mostly or entirely comprise a natural fiber such as cotton or wool. To avoid oxidation of such non-thermoplastic materials, heating can take place in an anoxic or low oxygen environment.

In production, precast 100 is placed over a positive mold and heated, such that at least some of the thermoplastic material(s) fuse, in what will become a rigid shell. This allows the shell portion to closely conform to whatever part(s) of the patient are to be motion-restrained.

Precast 100 has a tubular configuration, with superior and inferior open ends as depicted in FIG. 1. However, the corresponding orthosis can also open and close laterally, using a Velcro™ or similar hook and loop fastener 151, which can be installed at the precast stage. All suitable fasteners are contemplated, including buttons, toggles, studs, snap fastener, poppers, buckles, zippers, frogging, hooks and eyes, magnets, grommets, brooches, safety pins, fabric ties, and laces.

In FIG. 1, the flexible portions 120, 122 can advantageously be elastic, and in especially preferred embodiments, portions 120, 122 can be knitted to be increasingly flexible and/or elastic towards the outer edges. Such variance in flexibility and elasticity can promote wearer comfort by transitioning pressure against the body.

The flexible portions 120 and 122 are preferably elastic even after the heating and cooling processes. Elasticity is advantageous because it causes the corresponding orthosis to conform to different body shapes. Moreover, since the shell portion 110 of precast 100 only extends partway around the precast, flexibility of portion 124 could be sufficient to allow a user to pull the corresponding orthosis over his/her head, as an alternative means of placement.

Precast 100 includes a strap 140 to further secure the corresponding orthosis on a patient's body.

Figure 2:
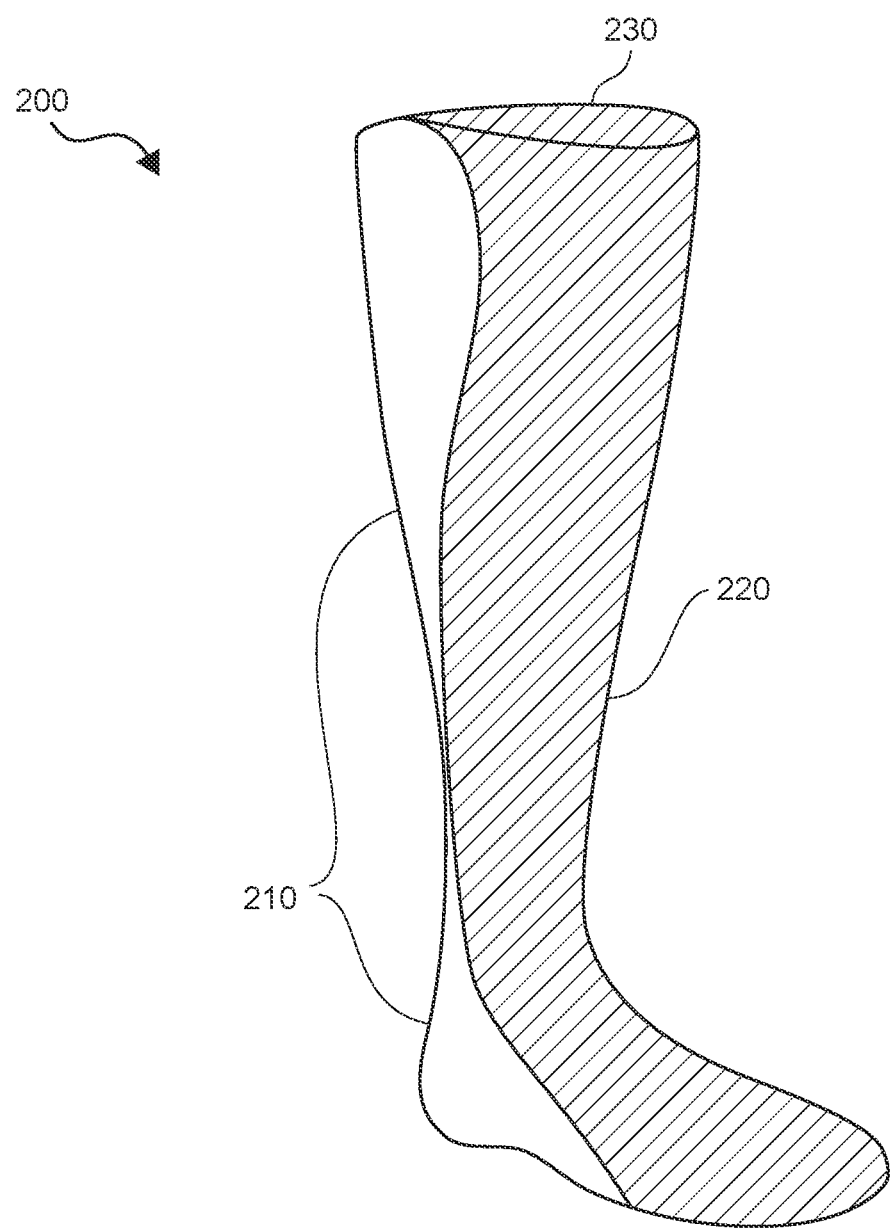
FIG. 2 is a perspective view of a precast of a leg-ankle-foot orthosis, according to inventive principles herein.

FIG. 2 generally depicts a precast 200, which can be heated and cooled to produce an orthosis configured to restrict movement of lower leg of a patient relative to the foot. Precast 200 generally includes a shell 210 and a flexible 220 portion, generally configured as a long sock, a tube 230 having an open upper calf end and a closed toe end. The precast 200, could also be provided in a preformed condition, in an average shape of a given anatomical size. Various sizes could be offered accordingly. This pre-shaped item could be commercially offered as an "off-the-shelf" product that could be provisioned to a patient of average contours given their dimensions without modification. It could also provide the opportunity for optimization of the contours through heating and reforming the shell material(s) in strategic locations.

In a corresponding orthosis 200, the shell 210 and flexible 220 portions cooperate to support posterior and anterior parts of the lower leg respectively. The shell 210 and the flexible 220 portions are oriented lengthwise along the tube 230. In this configuration, the flexible portion 220 allows easy on-off of the corresponding orthosis, while the shell portion 210 provides dorsiflexion, plantarflexion, inversion, and eversion stability at the ankle.

Strategic use of elastic regions can enhance functionality. For example in FIG. 2, flexible portion 220 can be elastic, and such elasticity can function to press the shell portion 210 against the back of the leg, and that can assist in lifting the foot during swing phase of ambulation. In some embodiments, an orthosis derived from precast 200 can have a slightly dorsiflexed configuration such that when worn, the weight of the foot pulls the foot into a neutral (neither dorsiflexed or plantarflexed) or other desired configuration.

Figures 3A, 3B:
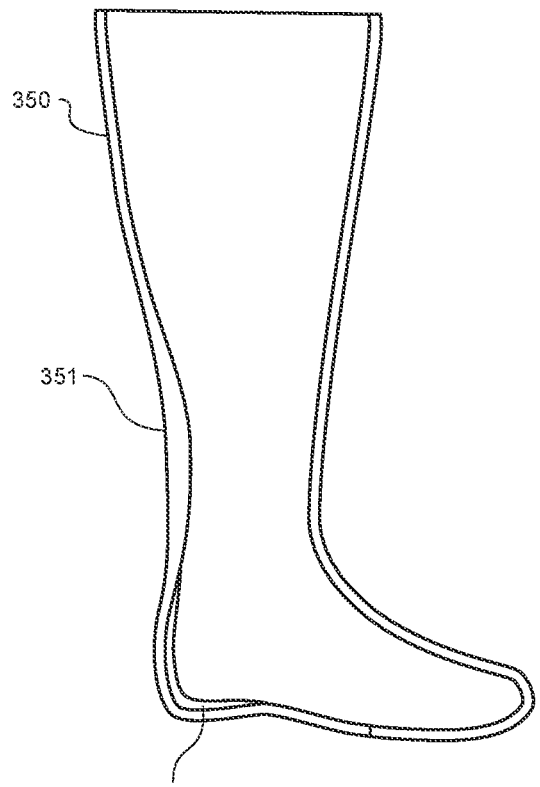
FIG. 3A is a perspective view of another precast of a leg-ankle-foot orthosis, according to inventive principles herein.
FIG. 3B is a vertical cross sectional view of the precast of FIG. 3A.

FIG. 3A generally depicts a precast 300 of a corresponding ankle foot orthosis. The shell portion 310 of the precast in FIG. 3A is wider (encompassing a greater amount of circumference) and potentially thicker than that in FIG. 2, which provides relatively greater (sagittal plane and coronal plane) stability to the ankle.

During the knitting process, the relative dimensions of the shell and flexible portions, and even areas of different thicknesses, can be easily customized, among other things to provide reinforcement where desired.

In FIG. 3B, for example, region 351 is knitted to be thicker than region 350. Thickness(es) can be customized by using different thermoplastic materials, different types or thicknesses of strands, and/or varying the knitting technique. As used herein, the term "knitting" should be interpreted very broadly to mean any means of producing a fabric substantially comprising one or more threads or yarns, for example including (1) a literal knitting ("V" shaped stiches), weaving (interlacing threads or yarns), crocheting (knot-like stitches) and macrameing (knot-like stiches in geometrical patterns).

Shell portions and flexible portions can be coupled in any suitable manner, including lateral juxtaposition and overlapping (the inside of a part of the shell portion 352 is layered/laminated with the flexible portion).

Figure 4:
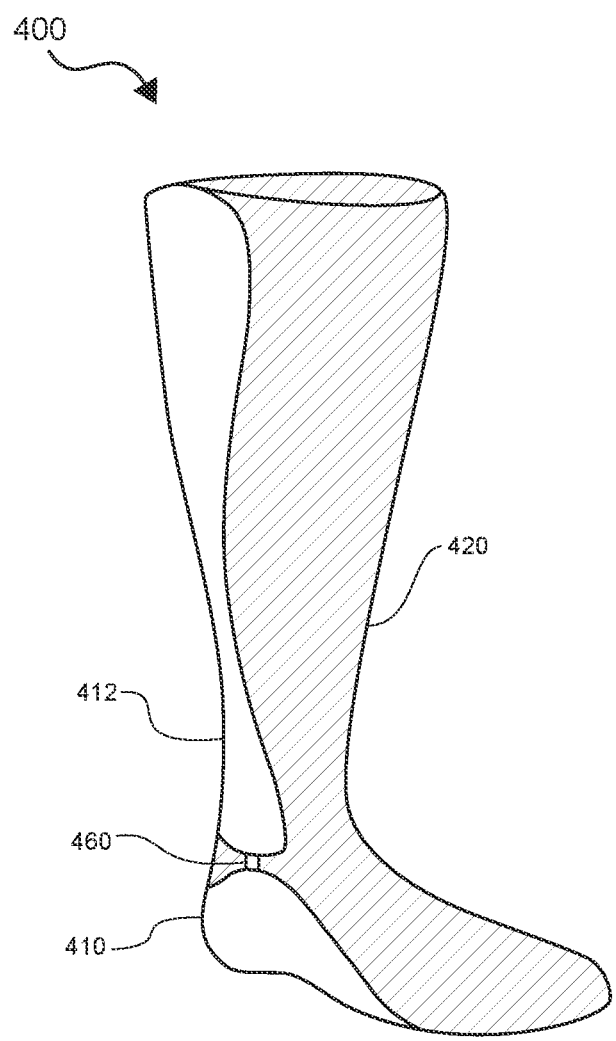
FIG. 4 is a perspective view of another precast of a leg-ankle-foot orthosis, according to inventive principles herein.

FIG. 4 generally depicts another precast 400 of a corresponding ankle foot orthosis. The precast has two shell portions, a lower shell portion 410 and an upper shell portion 412, and these two portions are at least partially coupled by a flexible portion 420 and/or by an additional flexible but inelastic connection 460. Flexible portion 420 may also be elastic. Relative to orthoses generated from the precasts 200, 300 of FIGS. 2 and 3, respectively, an orthosis generated from precast 400 would accommodate great ankle movements.

Figure 5:
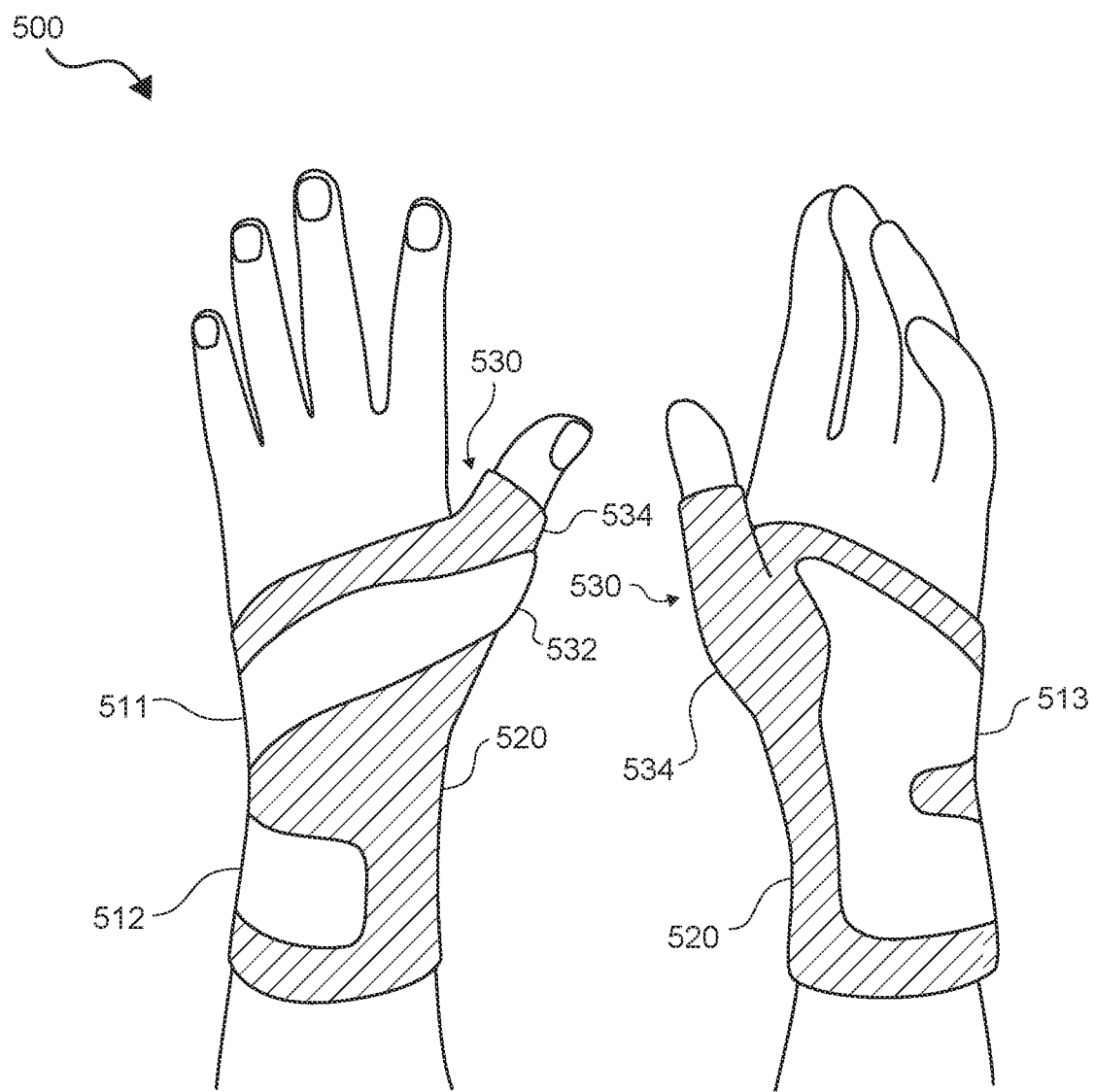
FIG. 5 is perspective views of dorsal and palmar views of a left person's left hand, wearing a precast of a wrist orthosis, according to inventive principles herein.

FIG. 5 generally depicts dorsal and palmar views of a left person's left hand, wearing a precast of a wrist orthosis 500. The shell portion appears as two physically separated regions 511, 512 on the dorsal side, but a single region 513 on the palmar side. The flexible portion 520 extends entirely around the shell portions 511, 512, and 513. On the orthosis for each hand, there are three openings, one for the thumb, one for the wrist, and one for the fingers/distal metacarpal region. In this particular example in this particular example, the thumb spica 530 includes a shell portion 532 and a flexible portion 534.

A wrist orthosis corresponding to precast 500 would be effective in reducing wrist flexion, extension, abduction, adduction and rotational movement, while still being relatively easy to put on because of the flexible portion 520.

Figure 6:
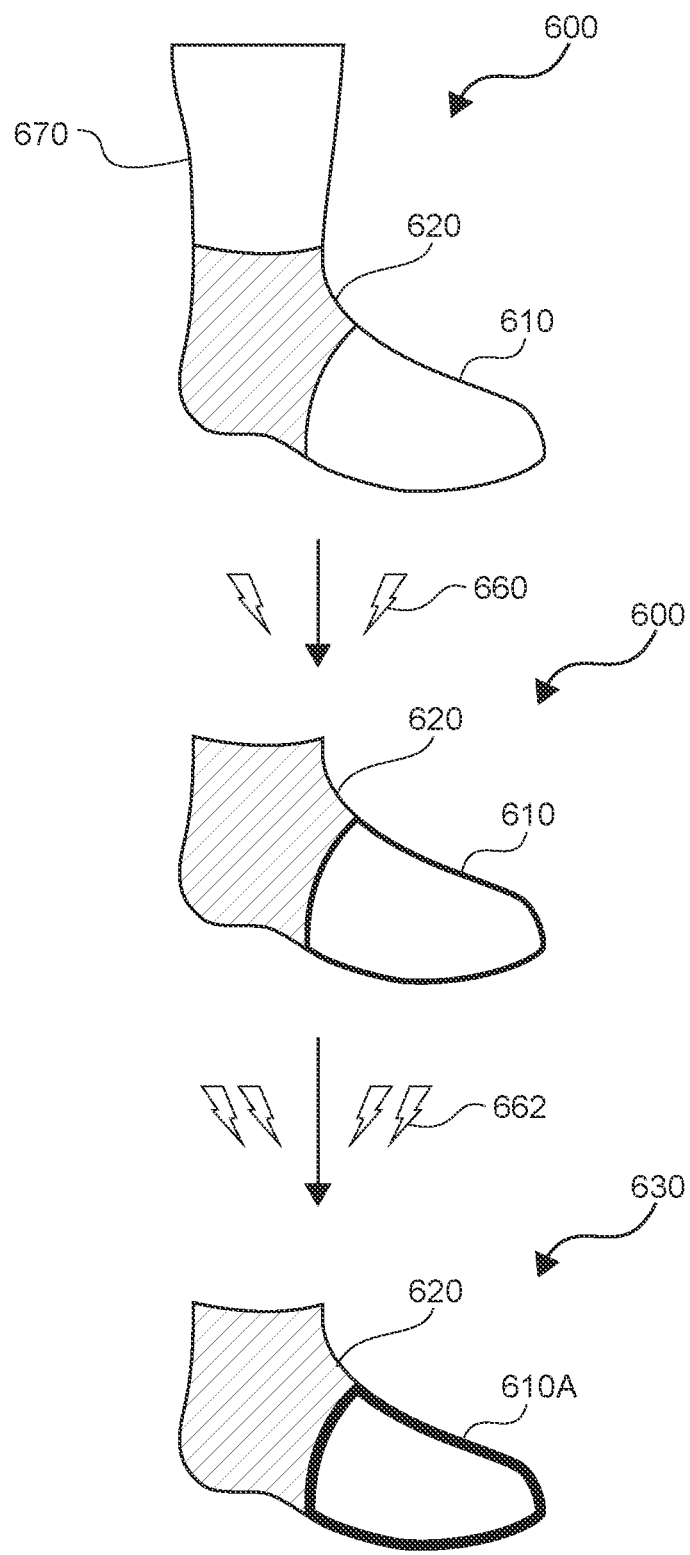
FIG. 6 shows a heating process of an embodiment of a precast, according to inventive principles herein.

FIG. 6 generally depicts stages in production of an orthotic from a knitted precast 600, without using a positive mold. The precast 600 includes knitted strands having at least two different thermoplastic materials, with one having a higher melting temperature than the other. The precast 600 is placed on the body part 670, and heated to a temperature 660 that partially melts the lower melting thermoplastic without injuring the person. This provides sufficient stiffness so that the precast 600 can retain its shape when carefully removed from the person. The stiffened precast 620 can then be hand molded if desired, and then heated to or the lower range of the melting point 662 of the higher melting point thermoplastic. Once cooled, the precast becomes ready to use orthosis 630, with now-hardened shell portion 610A.

Figures 7A, 7B:
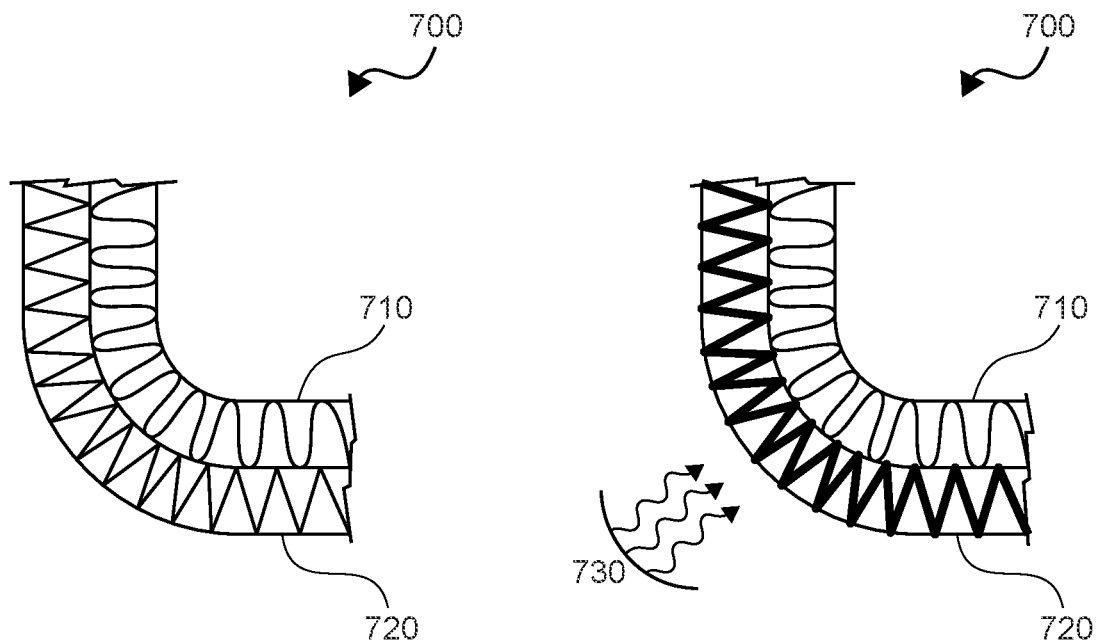
FIG. 7A is a schematic of a portion of an orthopedic precast, as for example in the precasts of FIG. 1, 2, 4, 5, or 6.
FIG. 7B is a schematic of the orthopedic precast portion of FIG. 7A, in which the thermoplastic material is heated.

FIG. 7A is a schematic of a portion of an orthopedic precast 700 having a first knitted portion 720 that includes thermoplastic material with a lower melting point than a second portion 710.

As with all examples herein where a first portion includes a thermoplastic material with a lower melting point than a second portion, it is contemplated that the difference in melting points can arise because the second portion has no melting point. In such cases, for example, the second portion could burn above the melting point of the thermoplastic material in the first portion (when in an oxygen environment), or pyrolyze above the melting point of the thermoplastic material in the first portion (when in an oxygen-free or oxygen-reduced environment), FIG. 7B is a schematic of the portion of an orthopedic precast 700 depicted in FIG. 7A, following heating at or above the lower range of the melting point of the thermoplastic material, followed by cooling to below the lower range of melting point of the thermoplastic material. Heating is provided by heat source 730, which should be interpreted as any suitable heat source, including but not limited to a steam generator.

Figures 8A, 8B:
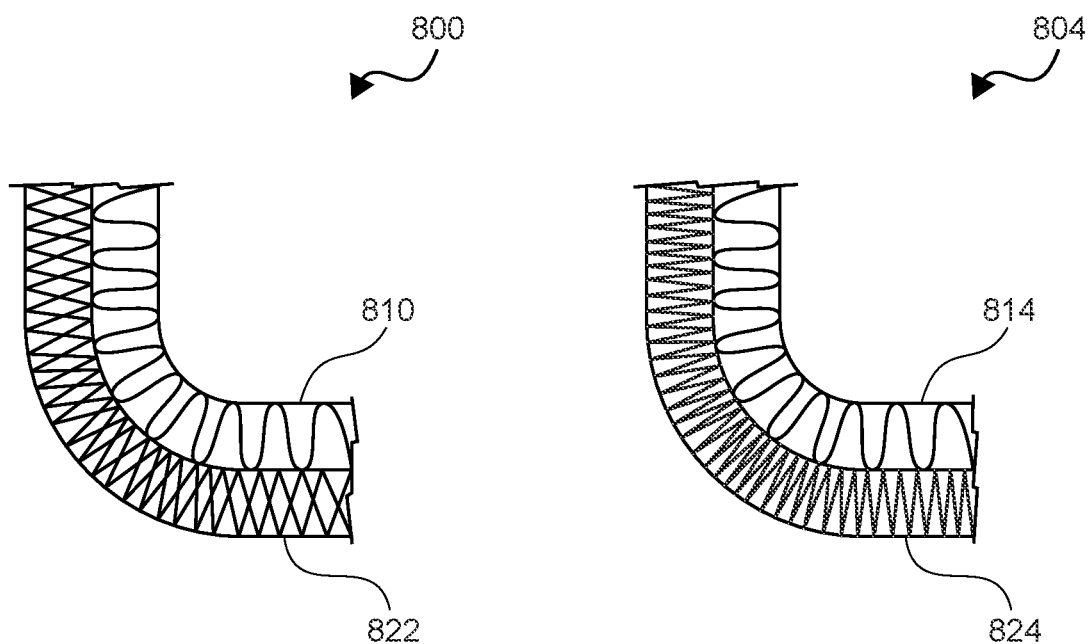
FIG. 8A is a schematic of a portion of an orthopedic precast having a first knitted portion configured with a higher concentration of a thermoplastic material than in a second portion.
FIG. 8B is a schematic of a portion of an orthopedic precast having a first knitted portion configured with a tighter knit than in a second portion.

FIG. 8A is a schematic of a portion of an orthopedic precast 800 having a first knitted portion 822 configured with a higher concentration of a thermoplastic material than in a second portion 810.

FIG. 8B is a schematic of a portion of an orthopedic precast 804 having a first knitted portion 824 configured with a tighter knit than in a second portion 814.

Figures 8C, 8D:
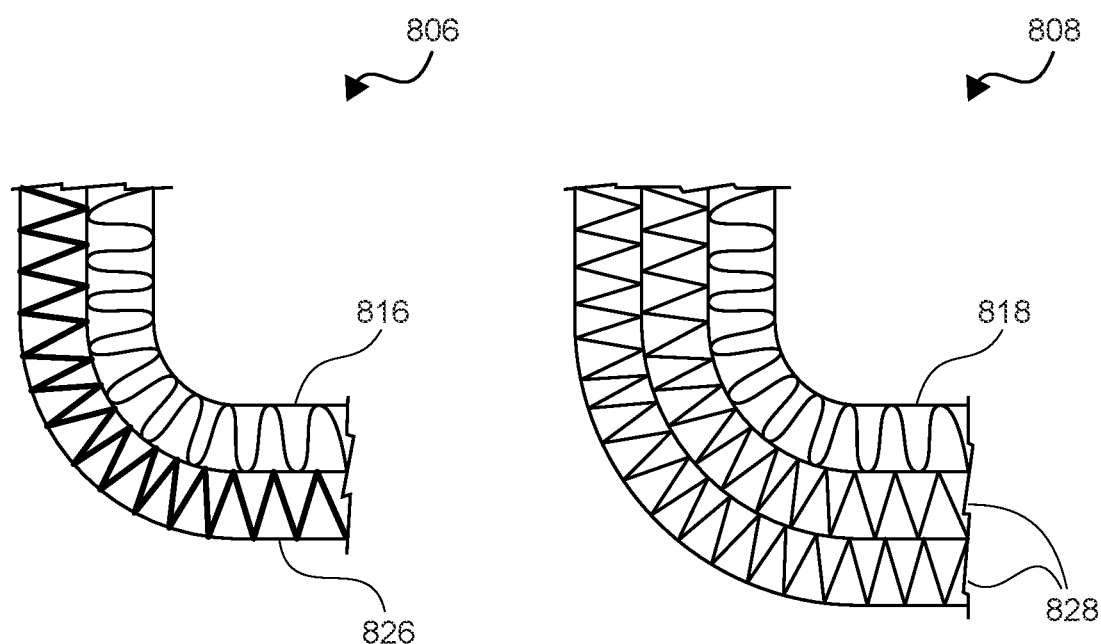
FIG. 8C is a schematic of a portion of an orthopedic precast having a first knitted portion configured with thicker filaments of a thermoplastic material than in a second portion.
FIG. 8D is a schematic of a portion of an orthopedic precast having a first knitted portion configured with a higher number of layers that include filaments of a thermoplastic material than in a second portion.

FIG. 8C is a schematic of a portion of an orthopedic precast 806 having a first knitted portion 826 configured with thicker filaments of a thermoplastic material than in a second portion 816.

FIG. 8D is a schematic of a portion of an orthopedic precast 808 having a first knitted portion 828 configured with a higher number of layers that include filaments of a thermoplastic material than in a second portion 818.

Figure 9:
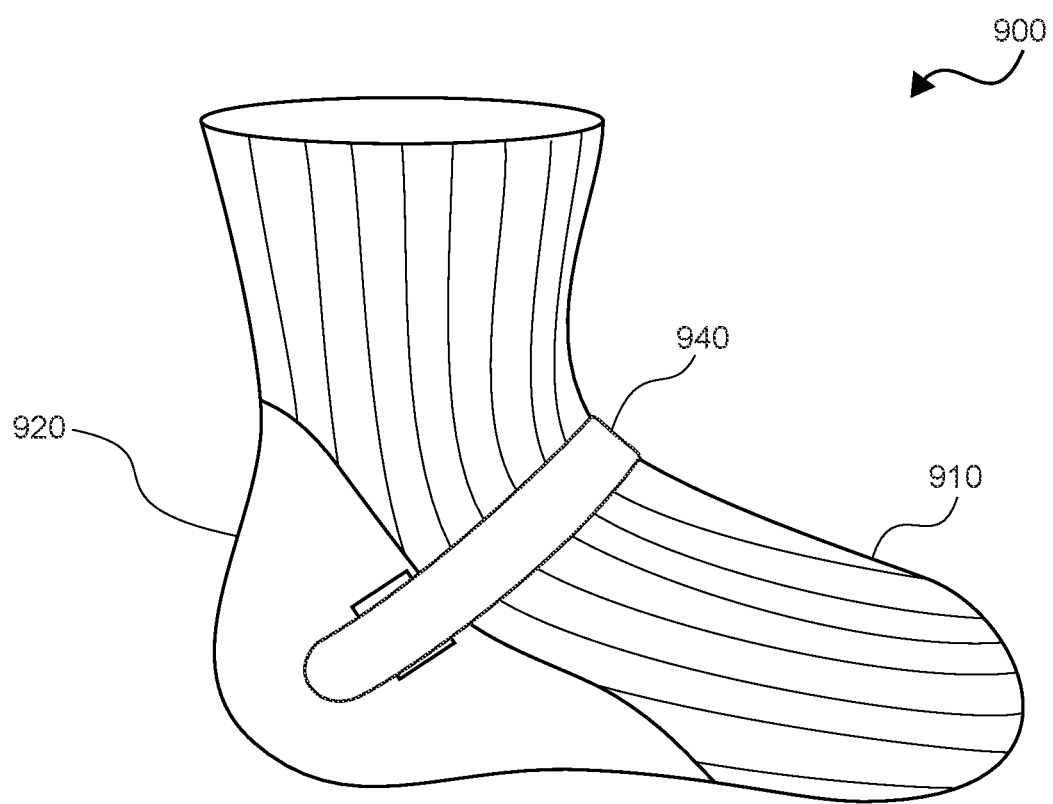
FIG. 9 is a schematic of a portion of an orthopedic precast having a strap.

FIG. 9 is a schematic of a portion of an orthopedic precast 900 having a first knitted portion 920 that includes a thermoplastic material with a lower melting point than a second portion 910. First knitted portion 920 also includes a material other than the thermoplastic material, that increases rigidity. Contemplated rigidity increasing materials include a carbon, glass or other rigid fibers. Second portion 910 includes Kevlar or other material having both high levels of strength and flexibility. Strap 940 is used to assist in retaining the orthopedic precast 900 on lower limb and foot of a wearer (not shown).

Figure 10A:
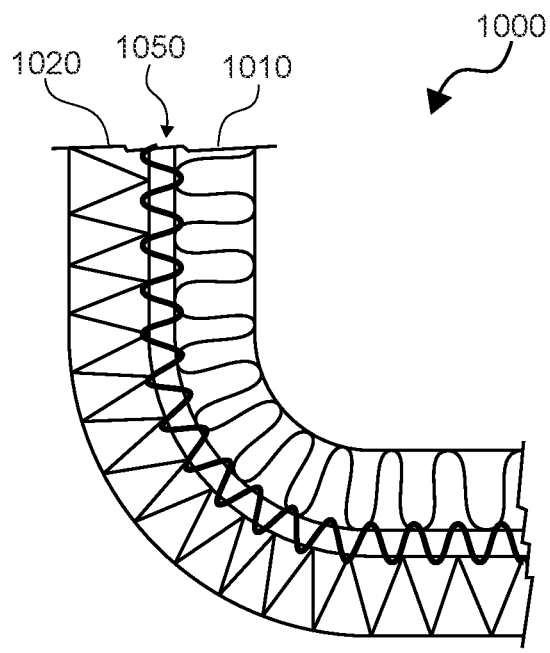
FIG. 10A is a schematic of a portion of an orthopedic precast in which a first knitted portion is sewn or knitted to a second portion.

FIG. 10A is a schematic of a portion of an orthopedic precast 1000 having a first knitted portion 1020 that includes a thermoplastic material with a lower melting point than a second portion 1010, in which the first portion 1020 is sewn or knitted 1050 to the second portion 1010.

Figure 10B:
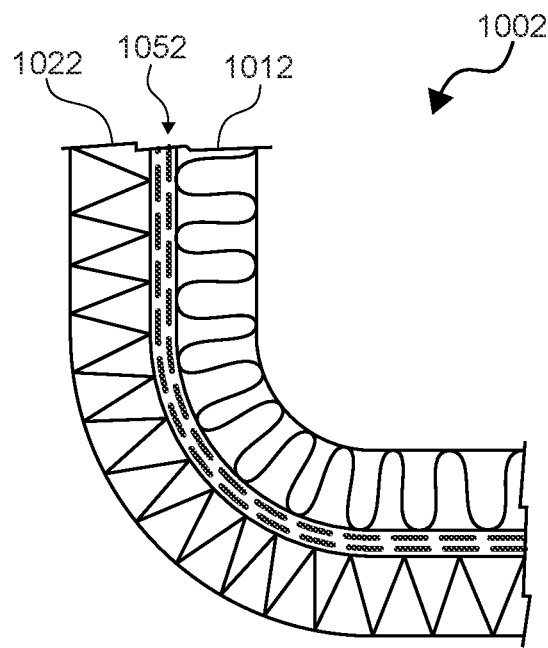
FIG. 10B is a schematic of a portion of an orthopedic precast in which a first knitted portion is laminated to a second portion.

FIG. 10B is a schematic of a portion of an orthopedic precast 1002 having a first knitted portion 1022 that includes a thermoplastic material with a lower melting point than a second portion 1012, in which the first portion 1022 is laminated to the second portion 1012 at lamination region 1052.

Figure 10C:
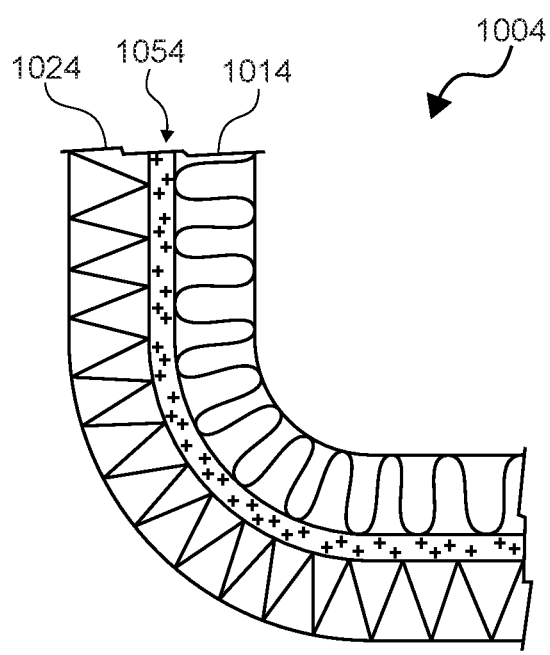
FIG. 10C is a schematic of a portion of an orthopedic precast in which a first knitted portion is chemically bonded to a second portion.

FIG. 10C is a schematic of a portion of an orthopedic precast 1004 having a first knitted portion 1024 that includes a thermoplastic material with a lower melting point than a second portion 1014, in which the first portion 1024 is chemical bonded to the second portion 1014 at chemical bonding region 1054.

Figure 10D:
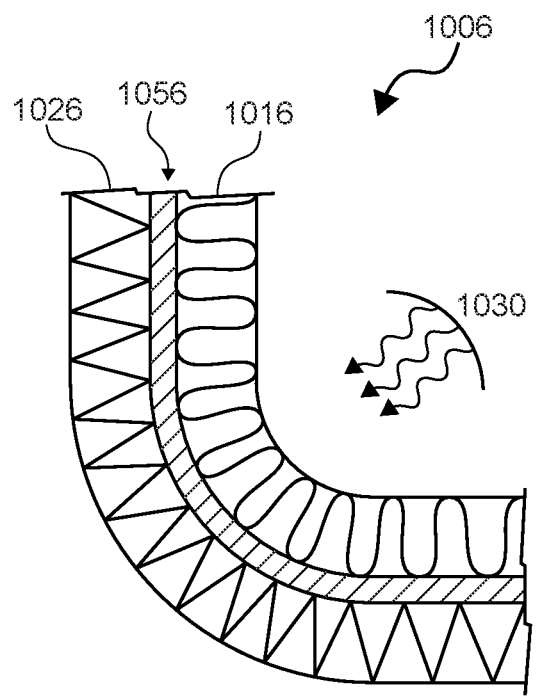
FIG. 10D is a schematic of a portion of an orthopedic precast in which a first knitted portion is partially melted and thereby fused to a second portion.

FIG. 10D is a schematic of a portion of an orthopedic precast 1006 having a first knitted portion 1026 that includes a thermoplastic material with a lower melting point than a second portion 1016, in which the first portion 1026 is melted to the second portion 1016 at melting region 1056, using heat provided by heat source 1030.

Figure 11:
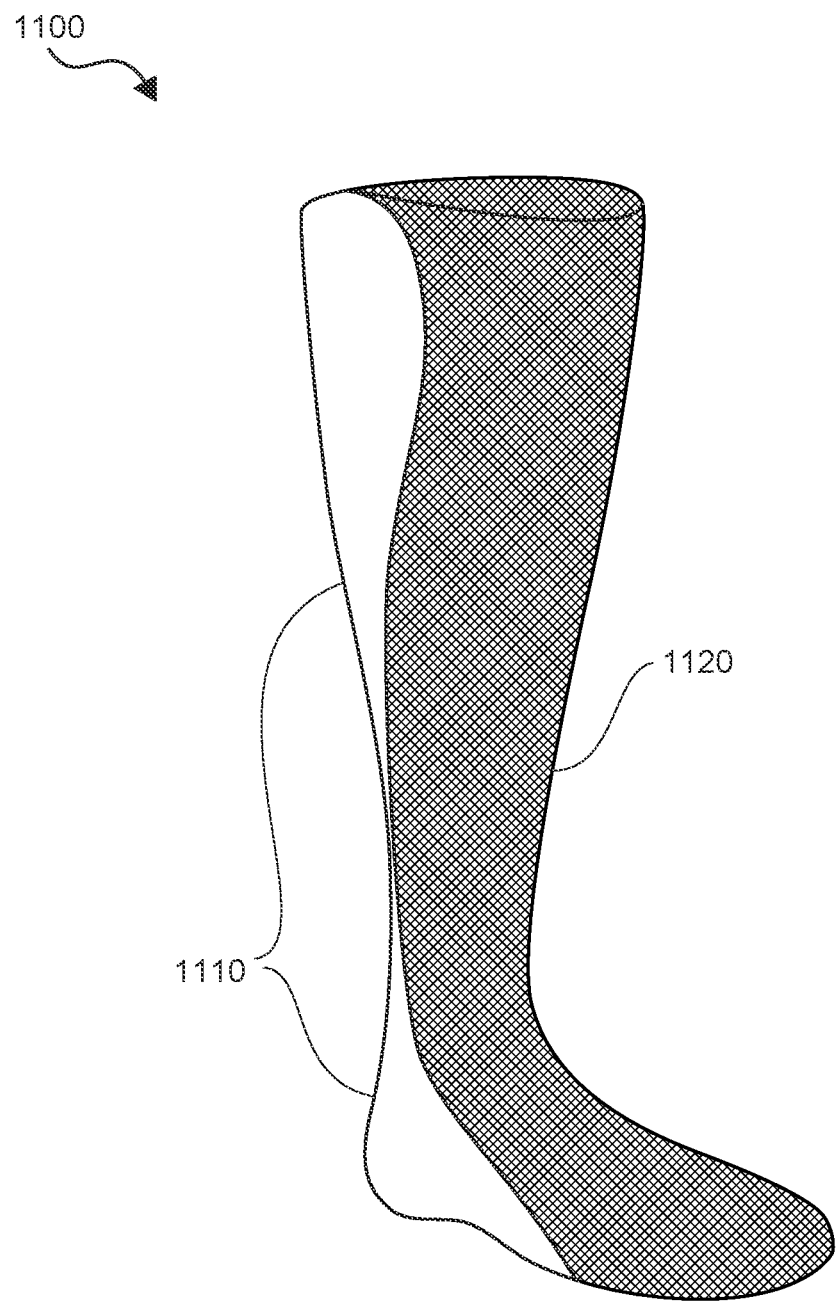
FIG. 11 is a perspective view of a portion of an orthopedic precast in which a first knitted portion is coupled with a second, elastic portion.

FIG. 11 is a perspective view of a portion of an orthopedic precast 1100 having a first knitted portion 1110 that includes a thermoplastic material with a lower melting point than a second portion 1120, in which the second portion 1120 is elastic. Elasticity can be accomplished via us of elastic threads and/or use of one or more knitting patterns that confer elasticity.

Figures 12A, 12B:
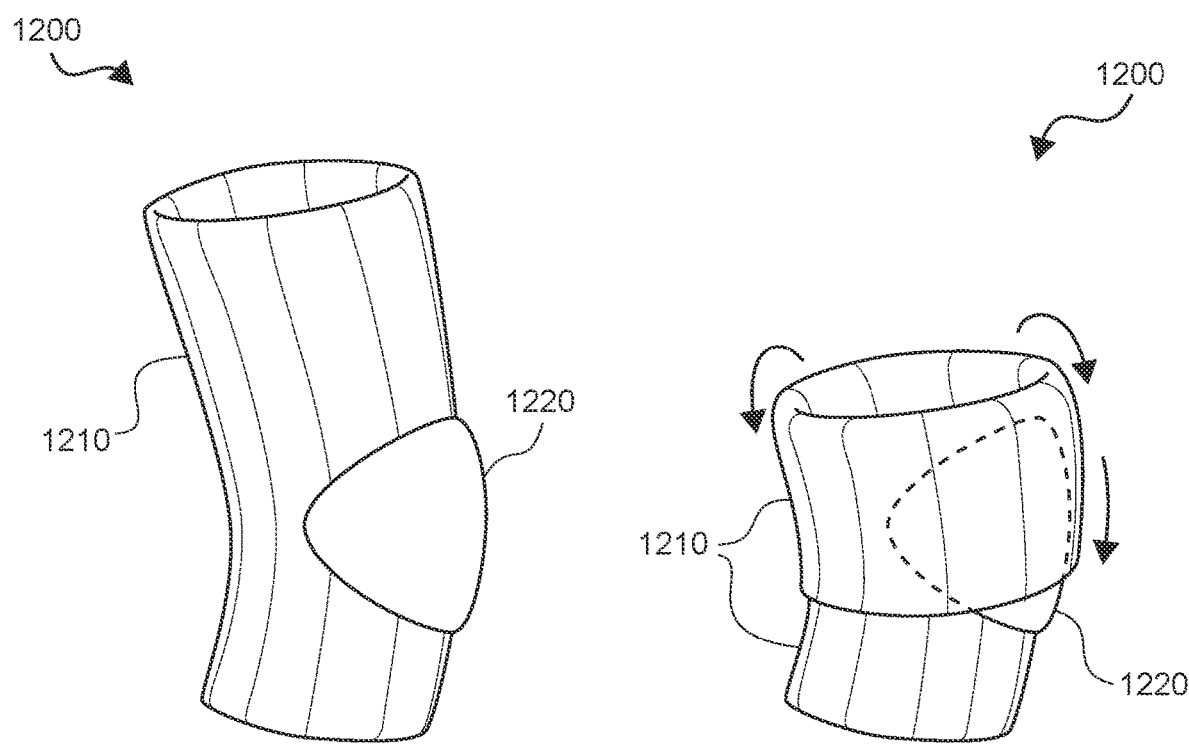
FIG. 12A is a perspective view of an orthopedic precast sleeve in which a first knitted portion is layered with a second portion.
FIG. 12B is a perspective view of the precast of FIG. 12A, in which a top portion of the sleeve has been folded down over part of the first knitted portion.

FIG. 12A is a perspective view of an orthopedic precast sleeve 1200 having a first knitted portion 1220 that includes a thermoplastic material with a lower melting point than a second portion 1210, in which the first portion 1220 layered with the second portion 1210.

FIG. 12B is a perspective view of the orthopedic precast 1200 depicted in FIG. 12A, in which the top of the sleeve has been folded down over part of the first knitted portion 1220. This is another example of how the first portion 1220 can be layered with the second portion 1210.

Figure 13:
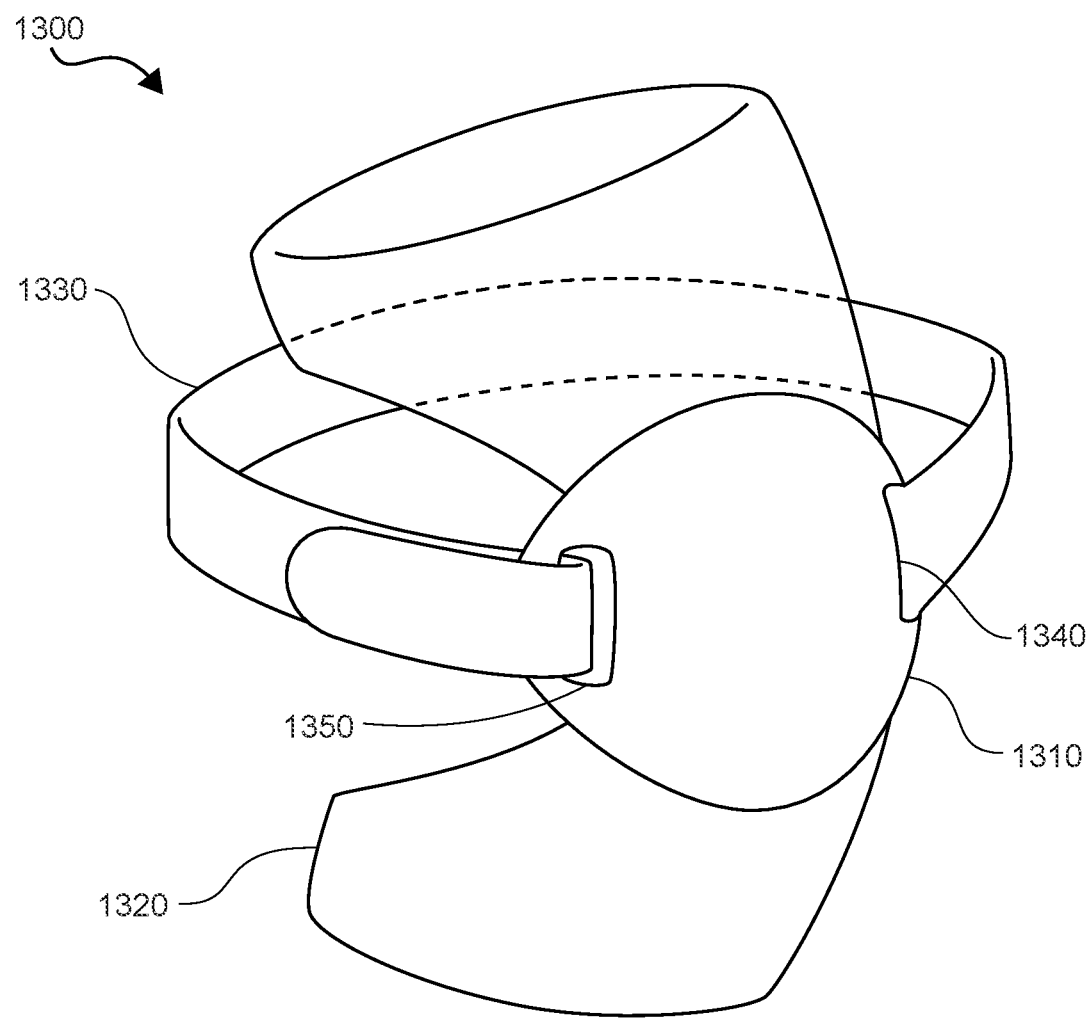
FIG. 13 is a perspective view of a portion of an orthopedic precast having a strap that extends through an eye.

FIG. 13 is a perspective view of an orthopedic precast 1300 having a first knitted portion 1310 that includes a thermoplastic material with a lower melting point than a second portion 1320. FIG. 13 also depicts a strap 1330, a portion of which passes through an eye 1350. Strap 1330 has footing 1340 at first knitted portion 1310.

Figure 14A:
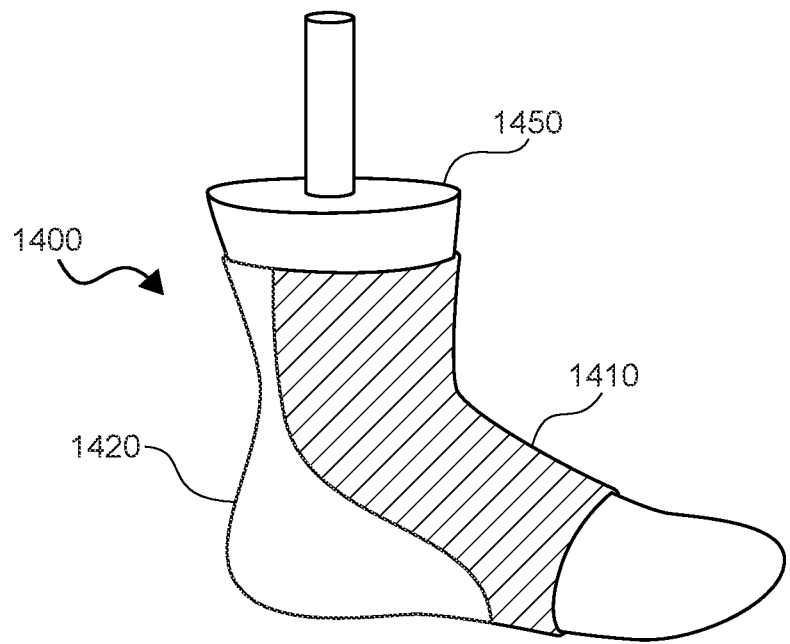
FIG. 14A is a perspective view of an orthopedic precast positioned about an inanimate mold.

FIG. 14A is a perspective view of an orthopedic precast 1400 having a first knitted shell portion 1420 that includes a thermoplastic material with a lower melting point than a second portion 1410. With precast 1400 positioned about a mold 1450, the precast 1400 is heated and then cooled to produce an orthopedic cast.

Figure 14B:
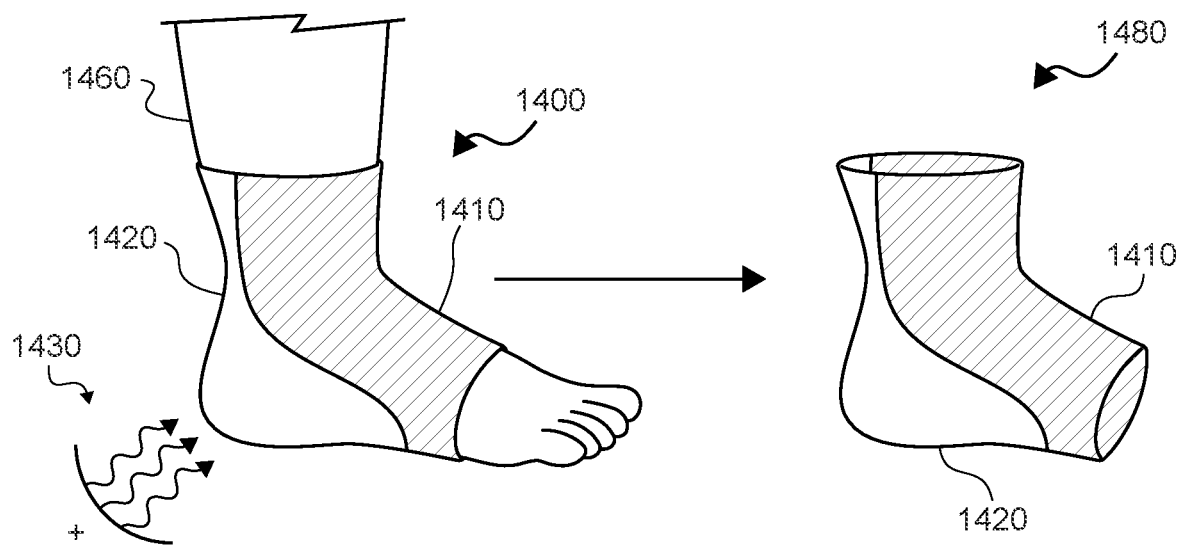
FIG. 14B is a perspective view of an orthopedic precast of FIG. 14A positioned about the lower leg, ankle and foot of a person along with an ankle-foot-orthosis (AFO) derived from the precast.

In FIG. 14B the mold 1460 is the lower leg, ankle and foot of a person. Precast 1400 is heated using heat source 1430 to at least a first melting point, and then cooled to at least partially melt and then at least partially rigidify the shell portion 1420 to produce the AFO orthosis 1480 of FIG. 14B.

FIG. 14C is a perspective view of an ankle-foot-orthosis (AFO) derived from the precast of FIG. 14B.

Figure 15:
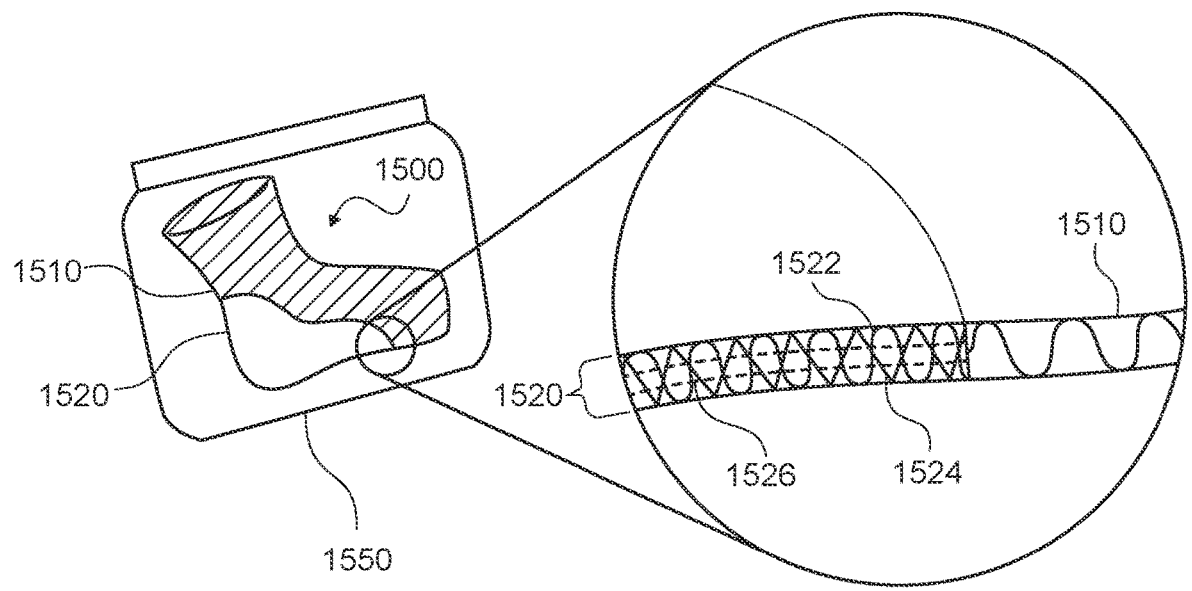
FIG. 15 is a perspective view of a self-heating, orthopedic precast disposed in a nitrogen filled bag, having embedded self-heating material.

FIG. 15 is a perspective view of a self-heating, orthopedic precast 1500 disposed in a nitrogen filled bag 1550. The precast 1500 has a shell portion 1520 with thermoplastic threads or yarns 1522, non-thermoplastic fibers 1524, and an amount of an embedded self-heating composition 1526. The embedded self-heating composition 1526 should be interpreted as any one or more of loose powder or other particles, particles bound to one or both of the thermoplastic threads or yarns 1522, and non-thermoplastic threads or yarns 1524 of the self-heating composition 1526. This particular example orthopedic precast 1500 is an AFO, in which the shell portion 1520 is knitted to a second, flexible portion 1510.

Any suitably functional material(s) can be employed as the embedded self-heating composition 1526, including for example, magnesium metal powder, alloyed with a small amount of iron, such as that used in heating meals-ready-to-eat (MREs). Typically such materials generate heat during an exothermic chemical reaction when triggered by oxygen in the atmosphere, and in FIG. 15, the embedded self-heating composition 1526 is prevented from doing so by being stored in a nitrogen-filled bag. In other contemplated embodiments, a suitable exothermic chemical reaction could be triggered in some other manner, such as by ambient heat or other light.

Upon removal of precast 1500 from the bag 1550, the precast 1500 is placed on a human limb or other mold, where the embedded self-heating composition 1526 comes in contact with oxygen in the air, and a chemical reaction heats the thermoplastic threads or yarns 1522 to around the melting point. Upon cooling, the thermoplastic threads or yarns 1522 partially melt together to form a hardened shell from portion 1520.

Figure 16:
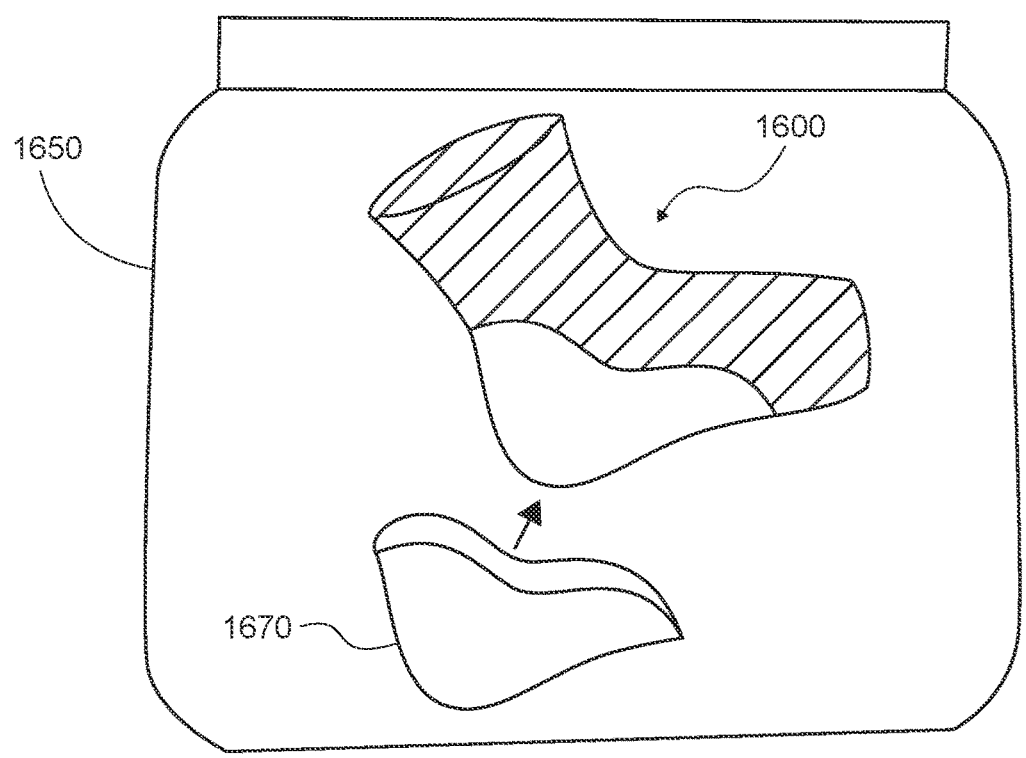
FIG. 16 is a perspective exploded view of an alternative self-heating, orthopedic precast disposed in a nitrogen filled bag, having self-heating material in an outer cover.

FIG. 16 is a perspective exploded view of an alternative self-heating, orthopedic precast 1600, similar to that in FIG. 15, except that here the self-heating composition is contained in an outer cover or blanket 1670, that is removable from the precast 1600.

Figure 17:
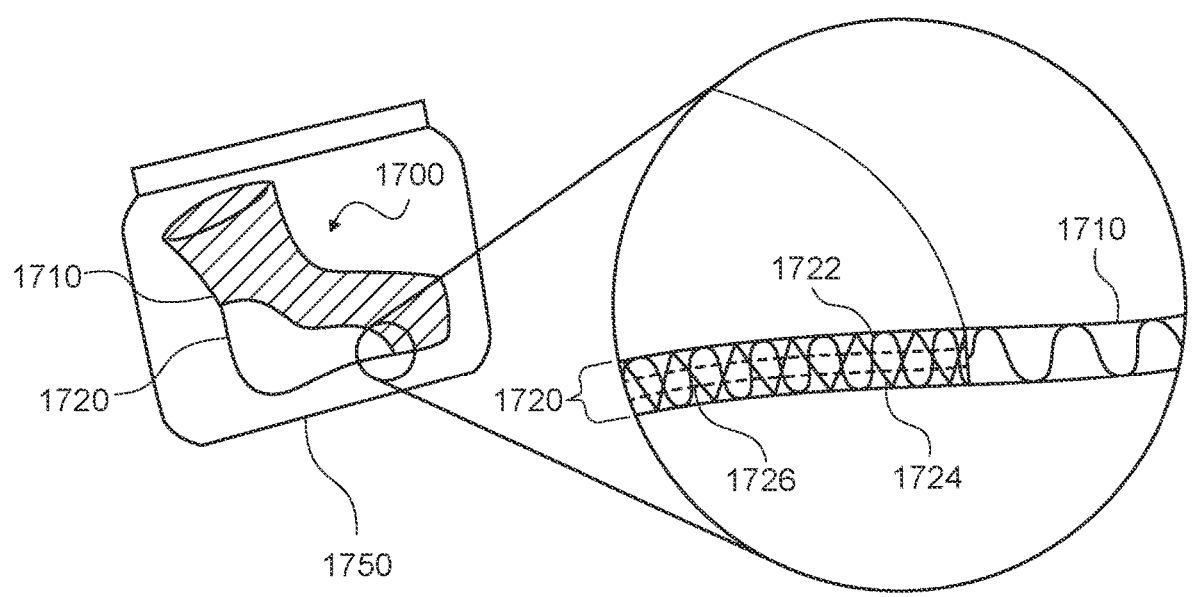
FIG. 17 is a perspective view of an alternative precast, which includes a polymerizable material. The precast is stored in a bag that excludes a polymerizing agent.

FIG. 17 is a perspective exploded view of yet another alternative orthopedic precast 1700, generally having a shell portion 1720 and a flexible portion 1710. The shell portion 1720 includes an amount of a polymerizable composition 1726, which should be interpreted as any one or more of loose powder or other particles 1726, threads or yarns 1722 that include polymerizable material, or particles of polymerizable material bound to any of the other threads or yarns 1724.

The precast 1700 is stored in bag 1750, which excludes a polymerizing agent. Contemplated polymerizing agents include, for example, UV or other light, one or more chemicals, or other suitable energy source. Upon opening of bag 1750, precast 1700 is placed on a human limb or other mold, and subject to the polymerizing agent to polymerize the polymerizable material 1726 to form a hardened shell from portion 1720.

It is still further contemplated instead of thermoplastic threads or yarns being heated and then cooled to form a shell portion, material could be used in the threads or yarns that is hardened by polymerization, with the polymerizing energy coming from ambient or artificial light, an oxidizing or reducing agent, or any other suitable energy source. FIG. 17

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A method of producing a custom orthosis for a patient, comprising:
   placing an orthopedic precast about a mold, the precast including a shell portion comprising at least a first knitted strand that includes at least a first thermoplastic material that at least partially melts at a first melting point, and a second portion comprising at least a second knitted strand that does not melt at or below the first melting point; and
   heating the precast on the mold to at least the first melting point to at least partially melt strands including at least the first thermoplastic material including at least the first knitted strand and subsequently cooling of the precast while on the mold as the shell portion becomes rigid.

2. The method of claim 1, wherein the precast comprises a tube that includes both the shell portion and the second portion, and further comprising pulling the tube over the mold.

3. The method of claim 1, wherein the mold about which the precast is molded is a positive mold, and further comprising forming a negative mold of a body part, and using the negative mold to produce the positive mold.

4. The method of claim 1, further comprising:
   adding including a second thermoplastic material into the knitted strand of the shell portion, the second thermoplastic material having a lower melting point than the first thermoplastic material; and
   heating the precast to a temperature that melts at least some of the second thermoplastic material without melting , but does not melt the first thermoplastic material.

5. The method of claim 1, further comprising selecting the first thermoplastic material such that the shell portion is resilient to bending.

6. A method of producing an orthosis, comprising:
   placing an orthopedic precast about a human limb or other mold, the orthopedic precast comprises a first knitted portion that includes a thermoplastic material configured to become hardened after application of a hardening agent to the first knitted portion, and a second knitted portion that remains flexible after the application of the hardening agent;

applying the hardening agent to the placed orthopedic precast to form an orthosis with a hardened portion formed by the first knitted portion and a flexible portion formed by the second knitted portion, and subsequently cooling the orthosis; and removing the orthosis from the mold.

7. The method of claim 6, wherein the applying of the hardening agent material further comprises applying heat to at least partially melt the thermoplastic material.

8. The method of claim 6, wherein the material includes a polymerizable composition, the hardening agent comprises a polymerizing agent, and further comprising applying the polymerizing agent sufficient to polymerize the polymerizable composition.

9. The method of claim 6, wherein the material configured to become hardened comprises strands of thermoplastic material and the hardening agent constitutes an application of heat.

10. The method of claim 6, wherein the applying of the hardening agent comprises generating heat by an exothermic chemical reaction caused by a self-heating composition included within including strands of the thermoplastic material that, upon exposure to ambient oxygen, causes the strands to at least partially melt.

11. The method of claim 6, wherein the material configured to become hardened includes a polymerizable composition, the hardening agent comprises a polymerizing agent, and further comprising applying the polymerizing agent sufficient to polymerize the polymerizable composition.

12. A method of producing a custom orthosis for a patient, comprising:

placing an orthopedic precast about a mold, the precast including a shell portion including first knitted strands that include at least a first thermoplastic material that at least partially melts at a first melting point, and a second portion including a second knitted strands with a second melting point significantly greater than the first melting point so that the first knitted strands can change phase and melt without changing a phase of the second knitted strands; and heating and then cooling the precast while about the mold to at least the first melting point to at least partially melt and rigidify the shell portion.

13. The method of claim 12, wherein the precast comprises a tube that includes both the shell portion and the second portion, and further comprising pulling the tube over the mold.

14. The method of claim 12, wherein the mold is a positive mold.

15. The method of claim 12, wherein the placing an orthopedic precast including forming the precast in which the shell portion further includes third knitted strands of a second thermoplastic material having a lower melting point than the first thermoplastic material; and the heating and then cooling of the precast comprises applying a temperature to the precast that melts at least some of the second thermoplastic material, but refraining from melting the first thermoplastic material associated with the first knitted strands.

16. The method of claim 12, further comprising selecting the first thermoplastic material such that the shell portion is resilient to bending.

17. The method of claim 12, wherein the precast includes a flexible portion, where an elasticity of the flexible portion operates to press the shell portion against a back of a leg of the patient and can assist in lifting a foot of the patient during a swing phase of ambulation by the patient.

18. The method of claim 17, wherein the precast is used to form an ankle foot orthosis.

* * * * *